United States Patent [19]

Cockerill et al.

[11] Patent Number: 5,605,912
[45] Date of Patent: Feb. 25, 1997

[54] CERTAIN PIPERDINO-2,4-DIENAMIDE PESTICIDES

[75] Inventors: George S. Cockerill, Milton Keynes; David A. Pulman, Berkeley; Robert J. Blade; Malcom H. Black, both of Herts, all of England

[73] Assignee: Roussel Uclaf, France

[21] Appl. No.: 321,843

[22] Filed: Oct. 14, 1994

Related U.S. Application Data

[62] Division of Ser. No. 991,239, Dec. 16, 1992, Pat. No. 5,380,733.

[30] Foreign Application Priority Data

Dec. 19, 1991 [GB] United Kingdom ............... 91-26955

[51] Int. Cl.$^6$ .................. A01N 43/40; C07D 211/06; C07D 405/08; C07D 405/12
[52] U.S. Cl. .................. 514/320; 514/329; 546/196; 546/205; 546/206; 546/309
[58] Field of Search .................. 546/226, 205, 546/206, 196; 514/329, 320

[56] References Cited

FOREIGN PATENT DOCUMENTS 0269457 6/1988 European Pat. Off. .
0369762 5/1990 European Pat. Off. .

OTHER PUBLICATIONS

Chemical Abstracts Service Registry Handbook, 1965–1971, CAS RN 103–80–0, 122–78–1, 625–40–1, 1184–53–8, 2345–38–2.
Chemical Abstracts Sevice Registry Handbook, 1965–1971, CAS RN 13910–23–1.
Chemical Abstracts Service Registry Handbook, 1974 Supplement, CAS RN 53304–24–8.
Chemical Abstracts Service Registry Handbook, 1976, CAS RN 60939–21–1.

Primary Examiner—Alan L. Rotman
Attorney, Agent, or Firm—Nixon & Vanderhye

[57] ABSTRACT

A compound of the formula:

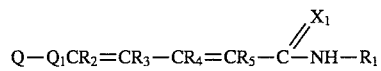

where Q is phenyl or naphthyl optionally substituted by (a) $C_{1-6}$ hydrocarbyl, $C_{1-6}$ alkoxy or methylenedioxy, which in turn is optionally substituted by one to five halogen atoms; or
(b) halo, cyano, nitro; or
(c) a group $S(O)_n R_7$ wherein n=0, 1, or 2 and $R_7$ is $C_{1-6}$ alkyl optionally substituted by halogen, or $R_7$ is amino optionally substituted by one or two $C_{1-6}$ alkyl groups; or a group $NR_8 R_9$ where $R_8$ and $R_9$ are independently selected from hydrogen, $C_{1-6}$ alkyl or a group $COR_{12}$ where $R_{12}$ is $C_{1-6}$ alkyl or $C_{1-6}$ alkoxy;

$Q_1$ is a 1,2-cyclopropyl ring optionally substituted by a group selected from $C_{1-13}$ alkyl, halo, $C_{1-3}$ haloalkyl or $C_{1-13}$ alkynyl or cyano;

$R_2$, $R_3$, $R_4$ and $R_5$ are the same or different with at least one being hydrogen and the others being independently selected from the group consisting of hydrogen, halo, $C_{1-4}$, alkyl or $C_{1-4}$ haloalkyl;

$X_1$ is oxygen or sulfur;

$R_1$ is a saturated 6 membered heterocycle containing a nitrogen atom which is bound to NH through a nitrogen atom and their use as pesticides, inecticides and acaricides.

5 Claims, No Drawings

CERTAIN PIPERDINO-2,4-DIENAMIDE PESTICIDES

This is a Rule 60 division of application Ser. No. 07/991, 239, filed Dec. 16, 1992 now U.S. Pat. No. 5,380,733.

This invention relates to pesticidal compounds, processes for their preparation, compositions containing them and to their use in the treatment of pests.

Unsaturated amides having a methylene chain of 1 to at least 10 carbon atoms optionally including at least one oxygen or additional methylene group are known as pesticides or insecticides having various terminating groups which include within their scope optiionally substituted phenyl (European Application Nos. 228222, 194764, 225011, Japanese Application No. 57-212150, Meisters and Wailes: Aust. J. Chem. 1966, 19, 1215, Vig et al: J. Ind. Chem, Soc. 1974, 51(9), 817) or pyridyl (European Application 269457) or fused bicyclic ring system (European Application Nos. 143593, 228853), dihalovinyl or optionally substituted ethynyl (European Application 228222).

EP 369762A discloses a cycloalkyl interstitial group linking the diene unit to the terminating group.

H. O. Huisman et al, Rev. trav. chim., 77, 97–102, (1958) discloses a group of 5-(2,6,6-trimethyl cyclohexenyl)2,4-pentadienamides as insecticides.

It has now surprisingly been discovered that certain novel unsaturated N-heterocyclic amides have utility as pesticides with improved properties over those where the amide group is an acyclic group.

Accordingly, the present invention provides a compound of formula (I):

$$Q(CH_2)_a(O)_bQ_1CR_2\!\!=\!\!CR_3\ CR_4\!\!=\!\!CR_5\ CX_1NHR_1$$

or a salt thereof where Q is an optionally substituted monocyclic or fused bicyclic ring system in which at least one ring is aromatic or Q is a dihalovinyl group or a group $R_6C\!\equiv\!C-$ where $R_6$ is $C_{1-4}$ alkyl, tri $C_{1-4}$ alkylsilyl, halo or hydrogen.

$Q_1$ is a 1,2-cyclopropyl ring optionally substituted by one or more groups selected from $C_{1-3}$ alkyl, halo, $C_{1-3}$ haloalkyl, $C_{1-3}$alkynyl, or cyano; or $Q_1$ is $(CH_2)_m$ wherein m=1 to 7; a=0 or 1; b=0 or 1;

$R_2$, $R_3$, $R_4$ and $R_5$ are the same or different with at least one being hydrogen and the others being independently selected from hydrogen, halo, $C_{1-4}$ alkyl or $C_{1-4}$ haloalkyl;

$X_1$ is oxygen or sulphur;

$R_1$ is a heteroaromatic or partially saturated five or six membered ring system containing a minimum of one and up to four hetero atoms independently selected from nitrogen, sulphur and oxygen, or $R_1$ is a saturated five or six membered ring system containing one or two heteroatoms independently selected from nitrogen, oxygen and sulphur.

$R_1$ is optionally substituted by 1 to 5 substituents selected from;

$C_{1-4}$ alkyl, $C_{1-4}$ alkoxy each optionally substituted by 1 to 5 halogen atoms; halogen, cyano, $C_{1-3}$ alkynyl, $C_{1-3}$ alkenyl, nitro, a group $(S(O)_nR_7$ wherein n=0, 1 or 2 and $R_7$ is $C_{1-4}$ alkyl optionally substituted by 1–5 halogens, a group $NR_8R_9$ wherein $R_8$ and $R_9$ are independently selected from hydrogen or $C_{1-4}$ alkyl, a group=$X_2$ where $X_2$=O, S or $NR_{10}$ where $R_{10}$ is selected from hydrogen, $C_{1-4}$ alkyl, $C_{1-4}$ alkoxy, and $COR_{11}$ where $R_{11}$ is $C_{1-4}$ alkyl.

Suitably $R_1$ is optionally substituted pyridine, furan, pyran, thiophene, pyrrole, pyrazole, imidazole, thiazole, oxazole, isoxazole, isothiazole, triazole, piperidine, morpholine, tetrahydropyran.

Suitably the substituents on the ring $R_1$ are $C_{1-4}$ alkyl, halo or $C_{1-4}$ alkyl substituted by 1–5 halo. Preferably the substituents are methyl, ethyl, chloro, fluoro or trifluoromethyl.

When Q is a ring system suitable substituents include $C_{1-6}$ hydrocarbyl, $C_{1-6}$ alkoxy or methylenedioxy, each optionally substituted by one to five halos, halo, cyano, nitro, or the substituent is a group $S(O)_nR_7$ wherein n is 0, 1 or 2 and $R_7$ is $C_{1-6}$ alkyl optionally substituted by one or more halos or $R_7$ is amino optionally substituted by one or two $C_{1-6}$ alkyl groups or the substituent is a group $NR_8R_9$ where $R_8$ and $R_9$ are independently selected from hydrogen, $C_{1-6}$ alkyl or a group $COR_{12}$ where $R_{12}$ is $C_{1-6}$ alkyl or $C_{1-6}$ alkoxy.

Suitably Q ia a ring system containing from 5 to 10 atoms containing a maximum of three heteroatoms selected from N, O or S and the rest carbon optionally substituted as above.

Suitably Q is phenyl, pyridyl, naphthyl or a fused bicyclic ring system containing a maximum of 3 heteratoms selected from N, O or S, each optionally substituted as defined above.

Preferably Q ia a monocyclic aromatic ring or fused bicyclic ring system of which at least onr ring is aromatic and containing 0 or 1 nitrogen atoms or 0 or 1 sulphur atoms.

When Q is a monocyclic aromatic ring, this is suitably phenyl, pyridyl thienyl and preferably phenyl. When Q is a bicyclic ring system, this is preferably naphthyl, quinolinyl, tetrahydronaphthyl or indanyl.

The Q ring system normally contains up to three substituents and is suitably unsubstituted or substituted by one, two or three substituents such as halo or $C_{1-5}$ haloalkyl such as trifluoromethyl. The substitution of the Q ring system depends upon the nature of this ring system but is preferably at the 3, 4 or 5 positions when Q is a 6-membered ring. Suitably $R_2$, $R_3$, $R_4$ and $R_5$ are chosen from hydrogen, methyl or fluoro. Suitably the stereochemistry of the double bonds is (E). Suitably when $R_3$ or $R_5$ is fluoro then the stereochemistry of the double bond to which $R_3$ or $R_5$ is attached is (Z).

Preferably $R_2$ is hydrogen, $R_3$ is hydrogen or fluoro, $R_5$ is hydrogen or fluoro and $R_4$ is hydrogen or $C_{1-4}$ alkyl, most preferably methyl.

Preferably $Q_1$ is a 1,2-cyclopropyl group or a group $(CH_2)_m$.

Preferably when $Q_1$ is a 1, 2-cyclopropyl ring, b=0; a=0.

Preferably the stereometric configuration of the cyclopropyl group in the chain is such that the groups Q and the carbon side-chain are attached to the ring to give trans geometry. Preferably the 3-position of the cyclopropyl ring is unsubstituted. Suitable substituents at the 1- and 2-positions of the cyclopropyl ring include fluoro, chloro, methyl or trifluoromethyl. Preferably the 2-position is unsubstituted and the 1-position is unsubstituted or substituted by fluoro or chloro.

When $Q_1$ is $(CH_2)_m$ and b=1, the value of m is preferabyl 6 when a=1 and preferably 7 when a=0.

One suitable group of compounds of the formula (I) is that of the formula (II):

$$Q_aQ_{1a}CR_{2a}\!\!=\!\!CR_{3a}CR_{4a}\!\!=\!\!CR_{5a}C(\!\!=\!\!X_{1a})\ NHR_{1a} \qquad (II)$$

or a salt thereof, wherein $Q_a$ is an optionally substituted phenyl or pyridyl group or an optionally substituted fused bicyclic ring system of which at least one ring is aromatic and containing 0 or 1 nitrogen atoms or 0 or 1 sulphur atoms.

$Q_{1a}$ is a 1,2-cyclopropyl ring optionally substituted by one or more groups selected from $C_{1-3}$ alkyl, halo, or $C_{1-3}$ haloalkyl;

$R_{2a}$, $R_{3a}$, $R_{4a}$ and $R_{5a}$ are the same or different with at least one being hydrogen and the others being independently selected from hydrogen, halo, $C_{1-4}$ alkyl and $C_{1-4}$ haloalkyl;

$X_{1a}$ is oxygen or sulphur; $R_{1a}$ is as hereinbefore defined for $R_1$.

When $Q_a$ contains an aromatic system, suitable substituents include one or more groups selected from halo, cyano, nitro, $C_{1-6}$ alkyl, $C_{1-6}$ alkoxy and methylenedioxy, each optionally substituted by one or more halos or the substituent is a group $S(O)_nR_{7a}$ wherein n is 0, 1 or 2 and $R_{7a}$ is $C_{1-6}$ alkyl optionally substituted by halo.

Preferably $Q_a$ is substituted phenyl or naphthyl or pyridyl.

Suitably $R_{2a}$, $R_{3a}$, $R_{4a}$ and $R_{5a}$ are chosen from hydrogen, methyl, or fluoro.

$R_{1a}$ is as hereinbefore defined.

The preferred group of compounds of the formula (II) includes those of formula (III):

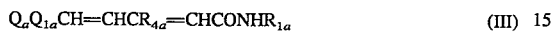

$$Q_aQ_{1a}CH=CHCR_{4a}=CHCONHR_{1a} \quad (III)$$

wherein $Q_a$, $Q_{1a}$, $R_{4a}$ and $R_{1a}$ are as hereinbefore described.

One preferred groups of compounds of the present invention includes those of formula (IV):

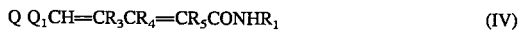

$$Q\ Q_1CH=CR_3CR_4=CR_5CONHR_1 \quad (IV)$$

wherein Q, $Q_1$, $R_4$ and $R_1$ are as hereinbefore described.

Preferred compounds of the formula (IV) include those wherein Q is substituted phenyl, $Q_1$ is a trans 1,2-cyclopropyl ring, where the 2-position of the cyclopropyl ring is unsubstituted or substituted by fluoro or chloro, $R_4$ is methyl or hydrogen, $R_3$ and $R_5$ are hydrogen or fluoro and $R_1$ is as hereinbefore defined.

By the term halo is meant fluoro, chloro, bromo and iodo.

By the term hydrocarbyl group is meant, alkyl, alkenyl, alkynyl, aralkyl including a cyclic alkyl or alkenyl group optionally substituted by alkyl, alkenyl or alkynyl; and alkyl or alkenyl substituted by cyclic alkyl and alkenyl, and phenyl groups.

Salts of the compounds of the present invention will normally be acid addition salts. Such salts may be formed from mineral or organic or cycloalkyl acids. Preferred salts include those formed from hydrochloric, hydrobromic, sulphuric, citric, nitric, tartaric, phosphoric, lactic, benzoic, glutamic, aspartic, pyruvic, acetic, succinic, fumaric, maleic, oxaloacetic, hydroxynaphthoic, isethionic, stearic, methanesulphonic, ethanesulphonic, benzenesulphonic, toluene-p-sulphonic, lactobionic, glucuronic, thiocyanic, propionic, embonic, naphthenoic and perchloric acids.

The compounds of formula (I) may exist in a number of stereoisomeric forms. The present invention encompasses both individual geometric and stereoisomers and mixtures thereof. The present invention also encompasses compounds of the formula (I) containing radioisotopes, particularly those in which one to three hydrogen atoms are replaced by tritium or one or more carbon atoms are replaced by $^{14}C$.

In a further aspect, the present invention provides a process for the preparation of a compound of the formula (I) as hereinbefore defined which comprises: either a) when $X_1$ is oxygen, the reaction of the corresponding acid or acid derivative $Q(CH_2)_a(O)_bQ_1CR_2=CR_3CR_4=CR_5C(=X)Z_1$ with an amine $H_2NR_1$ wherein Q, a, b, $Q_1$, $R_2$, $R_3$, $R_4$, $R_5$, and $R_1$ are as hereinbefore defined and X is oxygen and $Z_1$ is hydroxy, $C_{1-6}$ alkoxy, halo or a phosphoroimidate ester (—P(O)(O-aryl)NH— aryl where aryl is $C_{6-10}$ aryl); or b) the formation of the $CR_2=CR_3$ $CR_4=CR_5$ $C(=X_1)NHR_1$ moiety through a Wittig type reaction; and optionally thereafter converting one compound of the formula (I) into another compound of the formula (I) by methods well known to those skilled in the art.

Process (a) is normally carried out at a non-extreme temperature, for example between −25° and 150° C. in an anhydrous aprotic solvent, such as ether, dichloromethane, toluene or benzene. The precise conditions will be dependent on the nature of the group $Z_1$, for example when $Z_1$ is alkoxy the reaction is conveniently carried out at an elevated temperature, i.e. 50° to 125° C., and conveniently at reflux, preferably in the presence of a trialkylaluminium compound, such as trimethylaluminium, which forms a complex with the amine $H_2NR_1$. When $Z_1$ is halo or phosphoroimidate the reaction is conveniently carried out at −20° C. to 30° C. and preferably in the presence of a tertiary amine, such as triethylamine or pyridine.

If the acid derivative is an acid halide, for example the acid chloride, then it may be formed from the corresponding acid by reaction with a suitable reagent such as oxalyl chloride or thionyl chloride. When $Z_1$ is a phosphoroimidate group then this is suitably formed from $(PhO)P(O)NHPhCl$ where Ph is phenyl. The acid, or the acid function in the compound $Q(CH_2)_a(O)_bQ_1CR_2=CR_3CR_4=CR_5COZ_1$, may be prepared by hydrolysis of the corresponding ester.

The esters may be prepared by a number of alternative routes, for example:

(i) a conventional Wittig or Wadsworth-Emmons reaction, using for example an aldehyde and ethoxycarbonylmethylene triphenylphosphorane or an anion from triethylphosphonocrotonate or 3-methyl triethylphosphonocrotonate. This latter reaction may result in an isomeric mixture, for example a mixture of (Z) and (E) substituted dienoates; such a mixture may be reacted as above, and the resulting mixture of amides separated by chromatography or other convenient techniques. The Wittig-type reagent may be produced for example by the following route or a modification thereof:

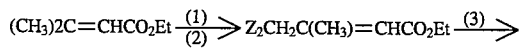

$$(CH_3)_2C=CHCO_2Et \xrightarrow{(1)}_{(2)} Z_2CH_2C(CH_3)=CHCO_2Et \xrightarrow{(3)}$$

Wittig/Wadsworth-Emmons reagent wherein $Z_2=(aryl)_3P$, $(aryl)_2P(O)$ or $(C_{1-4}$ alkoxy$)_2P(O)$ where aryl is preferably phenyl and alkoxy is preferably ethoxy.

(1) N-bromo succinimide
(2) e.g. $(EtO)_3P$ or $(Ph)_3P$
(3) This reaction is normally carried out in the presence of a base such as lithium diisopropylamide, butyllithium, sodium alkoxide or sodium hydride.

(ii) by rearrangement and elimination of $HS(—>O)Z_3$ from a compound of formula:

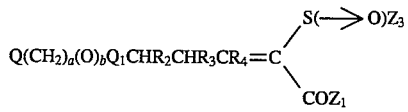

$$Q(CH_2)_a(O)_bQ_1CHR_2CHR_3CR_4=C\begin{array}{l}S(—>O)Z_3\\ \diagdown\\ COZ_1\end{array}$$

wherein Q, $Q_1$, $R_2$, $R_3$ and $R_4$ are as hereinbefore defined, $Z_3$ is any suitable group, eg phenyl, substituted phenyl such as 4-chlorophenyl or $C_{1-4}$ alkyl, for example methyl, $Z_1$ is as defined above, preferably $C_{1-4}$ alkoxy e.g. methoxy or ethoxy.

The above compound may be obtained by reaction of a compound $Q(CH_2)_a(O)_bQ_1CHR_2CHR_3CR_4O$ with a compound $Z_3 S(O)CH_2COZ_1$.

(iii) By elimination of $HOZ_5$ a compound $Q(CH_2)_a(O)_bQ_1CHR_2CR_3(OZ_5)CR_4=CR_5—COZ_1$ wherein Q, a, b, $Q_1$, $R_2$, $R_3$, $R_4$, $R_5$ and $Z_1$ are as defined above, and $Z_5$ is hydrogen or $C_{1-4}$ acyl such as acetyl. The reaction is preferably carried out in an aromatic solvent, conveniently in the presence of a molybdenum catalyst and a base, such as bis-trimethylsilylacetamide.

The above compound may be obtained by the reaction of a suitable aldehyde with a suitable sulphenyl compound, followed by acylation.

(iv) reaction of a compound of formula $Q(CH_2)_a(O)_bQ_1CR_2=CR_3C(=O)R_4$ with one of formula $Me_3SiCHR_5COZ_1$, wherein Q, a, b, $R_2$ to $R_5$, $Q_1$ and $Z_1$ are as hereinbefore defined.

This process may be carried out in an anhydrous solvent, e.g. tetrahydrofuran in the absence of oxygen, in the presence of a base, e.g. lithium cyclohexylisopropylamide.

(v) by reaction of a compound of formula $Q(CH_2)_a(O)_bQ_1CR_2=CR_3C(OZ_6)=CR_5COZ_1$ with a compound of formula $R_4M_1$ wherein Q, a, b, $Q_1$, $R_2$, $R_3$, $R_4$, $R_5$ and $Z_1$ are as hereinbefore defined, $Z_6$ is a suitable group such as dialkylphosphate or trifluoromethanesulphonate and $M_1$ is a metal such as copper (I) or copper (I) associated with lithium or magnesium.

This process can be performed at low temperature in an anhydrous ethereal solvent such as diethyl ether, dimethyl sulphide or tetrahydrofuran in the absence of oxygen.

(vi) by reaction of a compound of formula $Q(CH_2)_a(O)_bQ_1CR_2=CR_3M_2$ with one of formula $YCR_4=CR_5COZ_1$, wherein Q, a, b, $Q_1$, $R_2$, $R_3$, $R_4$, $R_5$ and $Z_1$ are as hereinbefore defined, Y is halo or tin and $M_2$ is a silyl or metal containing group, such as trimethylsilyl or a group containing zirconium, tin, aluminum or zinc, for example a bis(cyclopentadienyl) zirconium chloride group. This process is normally carried out at a non-extreme temperature i.e. between 0° and 100° C. and conveniently at room temperature, in a non-aqueous ethereal solvent such as tetrahydrofuran, in the presence of a palladium (O) catalyst, (such as bis (triphenylphosphine)palladium) and under an inert atmosphere of nitrogen or argon.

(vii) by elimination of $Z_3S$ (—>O)H from a compound of formula

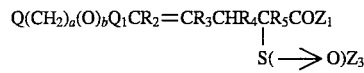

wherein Q, a, b, $Q_1$, $R_2$, $R_3$, $R_4$, $R_5$, $Z_3$ and $Z_1$ are as hereinbefore defined.

The above compound may be obtained by reaction of a compound $QQ_1CHR_2CR_3=CHR_4$ with $Z_3S(O)CH_2COZ_1$ Process (b) may be carried out by having an aldehyde or ketone group attached either to the amide/thioamide terminus or to the $QQ_1$ fragment of formula (I) and then reacting this with the appropriate phosphorous ylid.

i.e. $Q(CH_2)_a(O)_bQ_1(CR_2=CR_3)COR_4$ + $Z_2CHR_5.C(=X)NHR_1$ or $Q(CH_2)_a(O)_bQ_1COR_2$ + $Z_2CHR_3.CR_4=CR_5.C(=X)NHR_1$ or $Q(CH_2)_a(O)_bQ_1(CR_2=CR_3)CHR_5Z_2$ + $R_5CO.C(=X)NH.R_1$ wherein Q, a, b, $Q_1$, $R_2$, $R_3$, $R_4$, $R_5$, $R_1$, X and $Z_2$ are as hereinbefore defined.

Process (b) is carried out in an anhydrous inert solvent, for example an ether such as tetrahydrofuran or an alcohol such as methanol, optionally in the presence of a base, and preferably in the absence of oxygen, e.g. under a nitrogen atmosphere, at a low temperature (–60° to 20° C.). The phosphorous ylid may be obtained from its precursor as described above by reaction with a base such as lithium diisopropylamide, butyllithium, sodium alkoxide, sodium hydride, potassium or sodium carbonate. Compounds of the formula (I) wherein X is sulphur are preferably prepared by process (b) when $Z_2$ is a group $(C_{1-4}$ alkoxy)$_2P=O$.

Precursors of the type $Z_2CHR_3CR_4=CR_5(C=X_1)NHR$ are prepared according to the following route or a modification thereof when $X_1$=oxygen

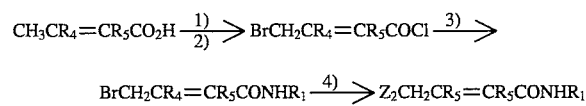

1) N-bromosuccinimide
2) thionyl chloride
3) $NH_2R_1$
4) $(EtO)_3P$ when $Z_2 = (OEt)_2P(O)-$ When $X_1$ is sulphur, precursors of the type $Z_2CHR_5(C=S)NHR_1$ are prepared from the reaction of the anion derived from $Z_2CH_2R_5$ with $R_1NCS$.

When $X_1$ is oxygen precursors of the type $Z_2CHR_5(C=O)NHR_1$ are prepared from the reaction of $Ph_3P$ or $P(OEt)_3$ with $ClCHR_5(CO)NHR_1$.

The aldehyde intermediates $Q(CH_2)_a(O)_bQ_1CR_2=O$ may be prepared by acid hydrolysis of a ketal, enol ether or acetal in a solvent such as acetone-water or by oxidation of the appropriate alcohols using for example pyridinium chlorochromate, pyridinium dichromate or oxalyl chloride-dimethyl sulphoxide in a solvent such as dichloromethane. The aldehydes may also be prepared by reduction of the appropriate nitriles with a reagent such as diisobutylaluminium hydride in hexane.

The intermediates of the present invention form a further aspect of the present invention and may be prepared where appropriate by standard methods other than those described.

The compounds of formula (I) may be used to control pests such as arthropods e.g. insect and acarine pests, and helminths, i.e. nematodes. Thus, the present invention provides a method for the control of arthropods and/or helminths which comprises administering to the arthropod and/or helminth or to their environment an arthropodically effective amount of a compound of the formula (I). The present invention also provides a method for the control and/or eradication of arthropod and/or helminth infestations of animals (including humans) and/or of plants, (including trees) and/or stored products which comprises administering to the animal or locus an effective amount of a compound of the formula (I). The present invention further provides for the compounds of the formula (I) for use in human and veterinary medicine, in public health control and in agriculture for the control of arthropod and/or helminth pests.

The compounds of formula (I) are of particular value in the protection of field, forage, plantation, glasshouse, orchard and vineyard crops, of ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g.

Urocerus) or beetles (e.g. scolytids, platypodids, lyctids, bostrychids, cerambycids, anobiids).

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of general formula (I) are of particular value in the control of arthropods or helminths which are injurious to, or spread or act as vectors of diseases in man and domestic animals, for example those hereinbefore mentioned, and more especially in the control of ticks, mites, lice, fleas, midges and biting, nuisance and myiasis flies.

The compounds of Formula (I) may be used for such purposes by application of the compounds themselves or in diluted form in known fashion as a dip, spray, fog, lacquer, foam, dust, powder, aqueous suspension, paste, gel, cream, shampoo, grease, combustible solid, vapourising mat, combustible coil, bait, dietary supplement, wettable powder, granule, aerosol, emulsifiable concentrate, oil suspensions, oil solutions, pressure-pack, impregnated article, pour on formulation or other standard formulations well known to those skilled in the art. Dip concentrates are not applied per se, but diluted with water and the animals immersed in a dipping bath containing the dip wash. Sprays may be applied by hand or by means of a spray race or arch. The animal, soil, plant or surface being treated may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material, such as that against which animals rub and transfer the material to their skins. Pour-on formulations are dispensed as a unit of liquid of small volume on to the backs of animals such that all or most of the liquid is retained on the animals.

The compounds of Formula (I) may be prepared either as formulations ready for use on the animals, plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powders and granules and other solid formulations comprise the compound of Formula (I) in intimate admixture with a powdered solid inert carrier for example suitable clays, kaolin, bentonite, attapulgite, adsorbent carbon black, talc, mica, chalk, gypsum, tricalcium phosphate, powdered cork, magnesium siliate, vegetable carriers, starch and diatomaceous earths. Such solid formulations are generally prepared by impregnating the solid diluents with solutions of the compound of formula (I) in volatile solvents, evaporating the solvents and, if desired grinding the products so as to obtain powders and, if desired, granulating, compacting or encapsulating the products.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates. Cationic emulsifiers include benzalkonium chloride and quaternary ammonium ethosuphates.

Amphoteric emulsifiers include carboxymethylated oleic imidazoline and alkyl dimethyl betain.

Vaporising mats normally comprise cotton and cellulose mix compressed into a board of approximately 35×22×3 mm dimensions, treated with up to 0.3 ml of concentrate comprising the active ingredient in an organic solvent and optionally an antioxidant, dye and perfume. The insecticide is vaporised using a heat source such as an electrically operated mat heater.

Combustible solids normally comprise of wood powder and binder mixed with the active ingredient and formed into shaped (usually coiled) strips. Dye and fungicide may also be added. Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively.

Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body. Suitably the plastics material is a polyvinyl chloride (PVC).

The concentration of the compound of Formula (I) to be applied to an animal, premises or outdoor areas will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% w/w except for undiluted formulations such as pour-on formulations which in general will be deposited at a concentration in the range from 0.1 to 20.0% and preferably 0.1 to 10%. The amount of compound to be applied to stored products in general will lie in the range of from 0.1 to 20 ppm. Space sprays may be applied to give an average initial concentration of 0.001 to 1 mg of compound of formula (I) per cubic meter of treated space.

The compounds of formula (I) are also of use in the protection and treatment of plant species, in which case an effective insecticidal, acaricidal or nematocidal amount of the active ingredient is applied. The application rate will vary according to the compound chosen, the nature of the formulation, the mode of application, the plant species, the planting density and likely infestation and other like factors but in general, a suitable use rate for agricultural crops is in the range 0.001 to 3 kg/Ha and preferably between 0.01 and 1 kg/Ha. Typical formulations for agricultural use contain between 0.0001% and 50% of a compound of formula (I) and conveniently between 0.1 and 15% by weight of a compound of the formula (I).

Dusts, greases, pastes and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca domestica*). In addition, certain compounds of formula (I) have activity against other arthropod pests including *Myzus persicae, Tetranychus urticae, Plutella xylostella, Culex spp. Tribolium castaneum, Sitophilus granarius, Periplaneta ameircana* and *Blattella germanica*. The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. Anobium, Ceutorhynchus, Rhynchophorus, Cosmopolites, Lissorhoptrus, Meligethes, Hypothenemus, Hylesinus, Acalymma, Lema, Psylliodes, Leptinotarsa, Gonocephalum, Agriotes, Dermolepida, Heteronychus, Phaedon, Tribolium, Sitophilus, Diabrotica, Anthonomus or Anthrenus spp.), Lepidoptera (e.g. Ephestia, Mamestra, Earias, Pectinophora, Ostrinia, Trichoplusia, Pieris, Laphygma, Agrotis, Amathes, Wiseana, Tryporysa, Diatraea, Sporganothis, Cydia, Archips, Plutella, Chilo, Heliothis, Spodoptera or Tineola spp.), Diptera (e.g. Musca, Aedes, Anopheles, Culex, Glossina, Simulium, Stomoxys, Haematobia, Tabanus, Hydrotaea, Lucilia, Chrysomia, Callitroga, Dermatobia, Gasterophilus, Hypoderma, Hylemyia, Atherigona, Chlorops, Phytomyza, Ceratitis, Liriomyza and Melophagus spp.), Phthiraptera (Malophaga e.g. Damalina spp. and Anoplura e.g. Linognathus and Haematopinus spp.), Hemiptera (e.g. Aphis, Bemisia, Phorodon, Aeneolamia, Empoasca, Parkinsiella, Pyrilla, Aonidiella, Coccus, Pseudococus, Helopeltis, Lygus, Dysdercus, Oxycarenus, Nezara, Aleurodes, Triatoma, Psylla, Mysus, Megoura, Phylloxera, Adelyes, Niloparvata, Nephrotetix or Cimex spp.), Orthoptera (e.g. Locusta, Gryllus, Schistocerca or Acheta spp.), Dictyoptera (e.g. Blattella, Periplaneta or Blatta spp.), Hymenoptera (e.g. Athalia, Cephus, Atta, Solenopsis or Monomorium spp.), Isoptera (e.g. Odontotermes and Reticulitermes spp.), Siphonaptera (e.g. Ctenocephalides or Pulex spp.), Thysanura (e.g. Lepisma spp.), Dermaptera (e.g. Forficula spp.), Pscoptera (e.g. Peripsocus spp.) and Thysanoptera (e.g. *Thrips tabaci*),.

Acarine pests include ticks, e.g. members of the genera Boophilus, Ornithodorus, Rhipicephalus, Amblyomma, Hyalomma, Ixodes, Haemaphysalis, Dermacentor and Anocentor, and mites and manges such as Acarus, Tetranychus, Psoroptes, Notoednes, Sarcoptes, Psorergates, Chorioptes, Eutrombicula, Demodex, Panonychus, Bryobia, Eriophyes, Blaniulus, Polyphagotarsonemus, Scutigerella, and Oniscus spp.

Nematodes which attack plants and trees of importance to agriculture, forestry, horticulture either directly or by spreading bacterial, viral, mycoplasma or, fungal diseases of the plants, include root-knot nematodes such as Meloidogyne spp. (e.g. *M. incognita*); cyst nematodes such as Globodera spp. (e.g. *G. rostochiensis*); Heterodera spp. (e.g. hydrogen. *avenae*); Radopholus spp. (e.g. *R. similis*); lesion nematodes such as Pratylenchus spp. (e.g. *P. pratensis*); Belonolaimus spp. (e.g. *B. gracilis*); Tylenchulus spp. (e.g. *T. semipenetrans*); Rotylenchulus spp. (e.g. *R. reniformis*); Rotylenchus spp. (e.g. *R. robustus*); Helicotylenchus spp. (e.g. hydrogen. *multicinctus*); Hemicycliophora spp. (e.g. hydrogen. *gracilis*); Criconemoides spp. (e.g. *C. similis*); Trichodorus spp. (e.g. *T primitivus*); dagger nematodes such as Xiphinema spp. (e.g. *X. diversicaudatum*), Longidorus spp (e.g. *L. elongatus*); Hoplolaimus spp. (e.g. hydrogen. *coronatus*); Aphelenchoides spp. (e.g. *A. ritzema-bosi, A. besseyi*); stem and bulb eelworms such as Ditylenchus spp. (e.g. *D. dipsaci*).

Compounds of the invention may be combined with one or more other pesticidally active ingredients (for example pyrethroids, carbamates and organophosphates) and/or with attractants, repellents, bacteriocides, fungicides, nematocides, anthelmintics and the like. Furthermore, it has been found that the activity of the compounds of the invention may be enhanced by the addition of a synergist or potentiator, for example: one of the oxidase inhibitor class of synergists, such as piperonyl butoxide or propyl 2-propynylphenylphosphonate; a second compound of the invention; or a pyrethroid pesticidal compound. When an oxidase inhibitor synergist is present in a formula of the invention, the ratio of synergist to compound of Formula (I) will be in the range 25:1–1:25 eg about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilises and as scavengers.

Industrial Applicability

Compounds of the present invention show increased pesticidal properties and/or photostability and/or reduced mammalian toxicity.

The following examples illustrate, in a non-limiting manner, preferred aspects of the invention.

| Formulations | |
|---|---|
| 1. Emulsifiable Concentrate | |
| Compound of formula (I) | 10.00 |
| Alkyl phenol ethoxylate* | 7.50 |
| Alkyl aryl sulphonate* | 2.50 |
| $C_{8-13}$ aromatic solvent | 80.00 |
| | 100.00 |
| 2. Emulsifiable Concentrate | |
| Compound of formula (I) | 10.00 |
| Alkyl phenol ethoxylate* | 2.50 |
| Alkyl aryl sulphonate* | 2.50 |
| Ketonic solvent | 64.00 |
| $C_{8-13}$ aromatic solvent | 18.00 |
| Antioxidant | 3.00 |
| | 100.00 |
| 3. Wettable Powder | |
| Compound of formula (I) | 5.00 |
| $C_{8-13}$ aromatic solvent | 7.00 |
| C18 aromatic solvent | 28.00 |
| China clay | 10.00 |
| Alkyl aryl sulphonate* | 1.00 |
| Napthalene sulphonic acid* | 3.00 |
| Diatomaceous earth | 46.00 |
| | 100.00 |
| 4. Dust | |
| Compound of formula (I) | 0.50 |
| Talc | 99.50 |
| | 100.00 |
| 5. Bait | |
| Compound of formula (I) | 0.5 |
| Sugar | 79.5 |
| Paraffin wax | 20.0 |
| | 100.00 |
| 6. Emulsion Concentrate | |
| Compound of formula (I) | 5.00 |
| $C_{8-13}$ aromatic solvent | 32.00 |
| Cetyl alcohol | 3.00 |
| Polyoxyethylene glycerol monooleate* | 0.75 |
| Polyoxyethylene sorbitan esters* | 0.25 |
| Silicone solution | 0.1 |
| Water | 58.9 |
| | 100.00 |

| Formulations | |
|---|---|
| 7. Suspension Concentrate | |
| Compound of formula (I) | 10.00 |
| Alkyl aryl ethoxylate* | 3.00 |
| Silicone solution | 0.1 |
| Alkane diol | 5.0 |
| Fumed silica | 0.50 |
| Xanthan gum | 0.20 |
| Water | 80.0 |
| Buffering agent | 1.2 |
| | 100.00 |
| 8. Microemulsion | |
| Compound of formula (I) | 10.00 |
| Polyoxyethylene glycerol monooleate* | 10.00 |
| Alkane diol | 4.00 |
| Water | 76.00 |
| | 100.00 |
| 9. Water Dispersible Granules | |
| Compound of formula (I) | 70.00 |
| Polyvinyl pyrrolidine | 2.50 |
| Alkyl aryl ethoxylate | 1.25 |
| Alkyl aryl sulphonate | 1.25 |
| China clay | 25.00 |
| | 100.00 |
| 10. Granules | |
| Compound of formula (I) | 2.00 |
| Alkyl phenol ethoxylate* | 5.00 |
| Alkyl aryl sulphonate* | 3.00 |
| $C_{8-13}$ aromatic solvent | 20.00 |
| Kieselguhr granules | 70.00 |
| | 100.00 |
| 11. Aerosol (pressure pack) | |
| Compound of formula (I) | 0.3 |
| Piperonyl butoxide | 1.5 |
| $C_{8-13}$ saturated hydrocarbon solvent | 58.2 |
| Butane | 40.0 |
| | 100.00 |
| 12. Aerosol (pressure pack) | |
| Compound of formula (I) | 0.3 |
| $C_{8-13}$ saturated hydrocarbon solvent | 10.0 |
| Sorbitan monooleate* | 1.0 |
| Water | 40.0 |
| Butane | 48.7 |
| | 100.00 |
| 13. Aerosol (pressure pack) | |
| Compound of formula (I) | 1.00 |
| $CO_2$ | 3.00 |
| Polyoxyethylene glycerol monooleate* | 1.40 |
| Propanone | 38.00 |
| Water | 56.60 |
| | 100.00 |
| 14. Lacquer | |
| Compound of formula (I) | 2.50 |
| Resin | 5.00 |
| Antioxidant | 0.50 |
| High aromatic white spirit | 92.0 |
| | 100.00 |
| 15. Spray (ready to use) | |
| Compound of formula (I) | 0.10 |
| Antioxidant | 0.10 |

13
-continued

| Formulations | |
|---|---|
| Odourless kerosene | 99.8 |
| | 100.00 |
| 16. Potentiated Spray (ready to use) | |
| Compound of formula (I) | 0.10 |
| Piperonyl butoxide | 0.50 |
| Antioxidant | 0.10 |
| Odourless kerosene | 99.30 |
| | 100.00 |
| 17. Microencapsulated | |
| Compound of formula (I) | 10.0 |
| $C_{8-13}$ aromatic solvent | 10.0 |
| Aromatic di-isocyanate# | 4.5 |
| Alkyl phenol ethoxylate* | 6.0 |
| Alkyl diamine# | 1.0 |
| Diethylene triamine | 1.0 |
| Concentrated hydrochloric acid | 2.2 |
| Xanthan gum | 0.2 |
| Fumed silica | 0.5 |
| Water | 64.6 |
| | 100.00 |

\* = Surfactant
# = react to form the polyurea walls of the microcapsule
Antioxidant could be any of the following individually or combined
Butylated hydroxytoluene
Butylated hydroxyanisole
Vitamin C (ascrobic acid)

The following Examples illustrate, in a non-limiting manner, preferred aspects of the invention.

EXPERIMENTAL

General Synthetic Methods and Procedures

Various compounds were synthesised and characterised in accordance with the following experimental procedures.

$^1$H NMR spectra were obtained on a Bruker AM-250 spectrometer in deuterochloroform solutions with tetramethylsilane as internal standard and are expressed as ppn from TMS, number of protons, number of peaks, coupling constant J Hz.

Progress of reactions could also be conveniently monitored on Aluminium sheets (40×80 mm) precoated with 0.25 mm layers of silica gel with fluorescent indicator and developed in appropriate solvent or solvent mixture. Temperature are in degrees. Celsius throughout.

Diethyl ether, hexane, ethanol, methanol, triethyamine, pyridine, magnesium sulphate and sodium hydroxide were obtained from BDH. Dichloromethane was obtained from Romil Chemicals and dimethylformamide from Rathburn Chemicals Ltd. 3-Amino-2-chloropyridine, 3-amino-pyridine, 2-aminopyridine, 4-aminopyridine, 2-amino-3-methylpyridine, 2-amino-thiazole, 3-amino-5-methylsoxazole, 2-amino-1,3,4-thiadiazole, 4-aminopyrimidine, 3-aminopyrazole, 1-aminopiperidine, 1-amino-2,6-dimethylpiperidine, 4-aminomorpholine, N-aminohexamethyleneimine and (+)-a-c-butyrolactone hydrochloride were obtained from Aldrich. 2-Amino-4-trifluoromethyl-1,3-thiazole and 2-amino-5-chloro-4-trifluoromethyl-1,3-thiazole were prepared as described by Wilkes M. C., Lavrik P. B., Greenplate J., J. Agric. Food. Chem., 39, 1652 (1991). The source of other chemicals is indicated in the text.

EXAMPLE 1

(+)-(2E,4E)-N-(2-chloro-3-pyridyl)-5-[c-2-(3,4-dibromophenyl)-r-1-fluorocyclopropyl]-penta-2,4-dienamide (i) (Z)-Ethyl 3-(3,4-dibromophenyl-2-fluoroprop-2-enoate was prepared by an analogous method to example 24 (EP 0 369 762 A1) from 3,4-dibromobenzaldehyde (example 14 EP 0 369 762 A1). NMR $^1$H: 1.2(3H, t)), 4.3(2H, q), 6.6(1H, d), 7.4(3H, m).

(ii) Ethyl (+)-5-[c-2-(3,4-dibromophenyl)-r-1-fluorocyclopropyl]penta-2,4-dienoate was prepared from the above by an analogous method to example 1 (EP 0 369 762 A1) using triethyl 4-phosphonocrotonate (ex Lancaster). NMR $^1$H: 1.3(3H, t), 1.6(1H, m), 2.3(1H, m), 4.2(2H, q), 5.8(1H, d), 5.9(1H, dd), 6.4(1H, dd), 7.0(1H, m), 7.3(1H, dd), 7.5(2H, m).

(iii) Ethyl (+)-5-[c-2-(3,4-dibromophenyl)-r-1-fluorocyclopropyl]penta-2,4-dienoate (3.5 g) in ethanol (50 ml) was stirred and heated to 50° C. A solution of sodium hydroxide (0.8 g) in water (5 ml) was added and heating continued for a further three hours. The solvent was removed under vacuum and water and diethyl ether were added. The aqueous solution was separated and acidified with dilute hydrochloric acid. The precipitate was extracted with diethyl ether, washed with brine and dried over magnesium sulphate. Removal of the solvent under vacuum gave (+)-5-[c-2-(3,4-dibromophenyl)-r-1-fluorocyclopropyl]-penta-2,4-dionoic acid (2.5 g). NMR $^1$H: 1.5(1H, m), 1.8(1H, m), 2.3(1H, m), 5.9(2H, m), 6.4(1H, dd), 7.0(1H, m), 7.3(1H, dd), 7.5(2H, m).

(iv) The above acid (350 mg) was suspended in dichloromethane (15 ml) and stirred under nitrogen at room temperature while oxalyl chloride (ex Aldrich) (156 mg/107 μl) and dimethylformamide (1 drop) were added. Stirring was continued for two hours and the solvent removed in vacuo. The remaining solid was dissolved in dichloromethane (20 ml), pyridine (100 μl) and 3-amino-2-chloropyridine (ex Aldrich) (158 mg) were added. After stirring overnight the organic solution was washed successively with 2N hydrochloric acid, saturated sodium hydrogen carbonate, brine and dried over magnesium sulphate. Removal of the solvent under vacuum gave a solid. Purification by chromatography (silica, ethyl acetate) gave the title compound (160 mg). Tlc (silica, ethyl acetate) Rf 0.7, m.pt. 181° C. NMR (DMSO) 1H: 1.8(1H, m), 2.1(1H, m), 2.7(1H, m), 6.5(3H, m), 7.3(2H, m), 7.5(1H, m), 7.8(2H, m), 8.4(2H, m), 9.9(1H, s).

EXAMPLE 2

(+)-(2E,4E)-N-(2-Thiazolyl)-5-[c-2-(3,4-dibromophenyl)-r-1-fluorocyclopropyl)penta-2,4-dienamide The title compound was prepared from 2-aminothiazole in an analogous manner to Example 1.

EXAMPLE 3

(+)-(2E/Z,4E)-N-Piperidino-5-[c-2-(3,4-dibromophenyl)-r-1-fluorocyclopropyl]-3-methylpenta-2,4-dienamide (2E:2Z=9:1)

The title compound was prepared from 1-aminopiperidine in an analogous manner to Example 1 but using triethylamine as base in the place of pyridine.

| Compound No. | Compound Name |
|---|---|
| 1. | (+)-(2E,4E)-N-(2-Chloro-3-pyridyl)-5-[c-2-(3,4-dibromophenyl)-r-1-fluorocyclopropyl]penta-2,4-dienamide |
| 2. | (+)-(2E,4E)-N-(3-Pyridyl)-5-[c-2-(3,4-dibromophenyl)-r-1-fluorocyclopropyl]-3-methylpenta-2,4-dienamide |
| 3. | (+)-(2E,4E)-N-(2-Pyridyl)-5-[c-2-(3,4-dibromophenyl)-r-1-fluorocyclopropyl]-3-methylpenta-2,4-dienamide |
| 4. | (+)-(2E/Z,4E)-N-(4-Pyridyl)-5-[c-2-(3,4-dibromophenyl)-r-1-fluorocyclopropyl]-3-methylpenta-2,4-dienamide (2E:2Z = 9,1) |
| 5. | (+)-(2E,4E)-N-(2-Chloro-3-pyridyl)-5-[c-2-(3,4-dibromophenyl)-r-1-fluorocyclopropyl]-3-methylpenta-2,4-dienamide |
| 6. | (+)-(2E,4E)-N-(3-Methyl-2-pyridyl)-5-[c-2-(3,4-dibromophenyl)-r-1-fluorocyclopropyl]penta-2,4-dienamide |
| 7. | (+)-(2E,4E)-N-(2-Thiazolyl)-5-[c-2-(3,4-dibromophenyl)-r-1-fluorocyclopropyl]penta-2,4-dienamide |
| 8. | (+)-(2E,4E)-N-(5-Methylisoxazole-3-yl)-5-[c-2-(3,4-dibromophenyl)-r-1-fluorocyclopropyl]penta-2,4-dienamide |
| 9. | (+)-(2E,4E)-N-(1,3,4-Thiadiazol-2-yl)-5-[c-2-(3,4-dibromophenyl)-r-1-fluorocyclopropyl]penta-2,4-dienamide |
| 10. | (+)-(2E,4E)-N-(4-Pyrimidyl)-5-[c-2-(3,4-dibromophenyl)-r-1-fluorocyclopropyl]penta-2,4-dienamide |
| 11. | (+)-(2E,4E)-N-(3-Pyrazolyl)-5-[c-2-(3,4-dibromophenyl)-r-1-fluorocyclopropyl]penta-2,4-dienamide |
| 12. | (+)-(2E,4E)-N-(4-Trifluoromethyl-1,3-thiazolyl)-5-[c-2-(3,4-dibromophenyl)-r-1-fluorocyclopropyl]penta-2,4-dienamide |
| 13. | (+)-(2E,4E)-N-2-(4-trifluoromethyl-5-chloro-1,3-thiazolyl)-5-[c-2-(3,4-dibromophenyl)-r-1-fluorocyclopropyl]penta-2,4-dienamide |
| 14. | (+)-(2E/Z,4E)-N-Piperidino-5-[c-2-(3,4-dibromophenyl)-r-1-fluorocyclopropyl]-3-methylpenta-2,4-dienamide (2E:2Z = 9:1) |
| 15. | (+)-(2E,4E)-N-Piperidino-5-[c-2-(3,4-dibromophenyl)-r-1-fluorocyclopropyl]penta-2,4-dienamide |
| 16. | (+)(2E,4E)-N-(2,6-Dimethylpiperidino)-5-[c-2-(3,4-dibromophenyl)--r-1-fluorocyclopropyl]penta-2,4-dienamide |
| 17. | (+)-(2E,4E)-N-Morpholino-5-[c-2-(3,4-dibromophenyl)-r-1-fluorocyclopropyl]penta-2,4-dienamide |
| 18. | (+)-(2E,4E)-N-(Perhydroazepin-1-yl)-5-[c-2-(3,4-dibromophenyl)-r-1-fluorocyclopropyl]penta-2,4-dienamide |
| 19. | (+)-(2E,4E)-N-(2-Oxotetrahydrofur-3-yl)-5-[c-2-(3,4-dibromophenyl)-r-1-fluorocyclopropyl]penta-2,4-dienamide |

| Compound No. | Wittig Reagent | Amine | EE:EZ a:b | Prepared according to Example No. |
|---|---|---|---|---|
| 1 | 1 | 3-Amino-2-chloropyridine | a | 1 |
| 2 | 2 | 3-Aminopyridine | a | 1 |
| 3 | 2 | 2-Aminopyridine | a | 1 |
| 4 | 2 | 4-Aminopyridine | 9:1 | 1 |
| 5 | 2 | 3-Amino-2-chloropyridine | a | 1 |
| 6 | 1 | 2-Amino-3-methylpyridine | a | 1 |
| 7 | 1 | 2-Aminothiazole | a | 2 |
| 8 | 1 | 3-Amino-5-methylisoxazole | a | 2 |
| 9 | 1 | 2-Amino-1,3,4-thiadiazole | a | 2 |
| 10 | 1 | 4-Aminopyrimidine | a | 2 |
| 11 | 1 | 3-Aminopyrazole | a | 2 |
| 12 | 1 | 2-Amino-4-trifluoromethyl-1,3-thiazole | a | 2 |
| 13 | 1 | 2-Amino-5-chloro-4-trifluoromethyl-1,3-thiazole | a | 2 |
| 14 | 2 | 1-Aminopiperidine | 9:1 | 3 |
| 15 | 1 | 1-Aminopiperidine | a | 3 |
| 16 | 1 | 1-Amino-2,6-dimethylpiperidine | a | 3 |
| 17 | 1 | 4-Aminomorpholine | a | 3 |
| 18 | 1 | N-aminohexamethyleneimine | a | 3 |
| 19 | 1 | (+)-a-Amino-c-butyrolactone hydrobromide | a | 3 |

Wittig Reagent
1 = triethyl 4-phosphonocrotonate
2 = triethyl 3-methyl-4-phosphonocrotonate

| Compound No. | m.pt. °C. | Mass Spectrum M + 1 |
|---|---|---|
| 1 | 181 | 499 |
| 2 | 163–6 | 479 |
| 3 | 155–6 | 479 |
| 4 | 107–8.5 | 479 |
| 5 | oil | 513 |
| 6 | 96–90 | 478 |
| 7 | 201.5 | 471 |
| 8 | 190–2 | 469 |
| 9 | 205.3. | 472 |
| 10 | 154.1 | 466 |
| 11 | 52.7 | 454 |
| 12 | 178–80 | 539 |
| 13 | 150.5 | 573 |
| 14 | 60.5 | 487 |
| 15 | 175–6 | 473 |
| 16 | 178.9 | 499 |
| 17 | 179.5 | 475 |
| 18 | 165.2 | 485 |
| 19 | 145–9 | 472 |

BIOLOGICAL DATA

The following examples illustrate, in a non-limiting manner, the pesticidal activity of compounds of formula (I):

EXAMPLE A—SPRAY TESTS

The activity of compounds of the invention were tested by dissolving the compounds in acetone (5%) and then diluting in water: "Synperonic" (94.5%:0.5%) to give a water emulsion. The solution was then used to treat the following insects, for which activity was observed at the following spray rates:

*Plutella xylostella*

Chinese cabbage leaf discs infested with 8 2nd instar *Plutella larvae* were sprayed with the solution containing the compound. Mortality was assessed after 2 days at 25° C..

The following compounds were active at 1000 pm or less:

1, 2, 3, 4, 5, 6, 8, 19

The following compounds were active at 200 ppm or less:

15, 16, 17, 18

Spodoptera littoralis

Uninfested leaves were sprayed with the test solution containing the compound and left to dry. These were then infested with 10 newly hatched larvae. Mortality was assessed after 3 days.

The following compounds were active at 1000 ppm or less:

3, 4, 9, 19

The following compounds were active at 200 ppm or less:

2, 5, 14, 15, 16, 17, 18

Diabrotica undecimpunctata

Filter paper and diet were sprayed with the test solution and then infested with 8 2nd instar larvae. Activity was assessed at 2 days.

The following compounds were active at 1000 ppm or less:

1, 3, 5, 14, 15, 16, 17, 18

Tetranychus urticae

French bean leaf discs infested with mixed stages of mites were sprayed with the solution containing the compound. Mortality was assessed after 2 days.

The following compounds were active of 1000 ppm or less:

5, 14, 18

Myzus perticae

Chinese cabbage leaf discs infested with 10 adult Myzus were sprayed with the solution containing the compound. Mortality was assessed after 2 days.

The following compounds were active at 1000 ppm or less:

5, 14, 16

EXAMPLE B—TOPICAL APPLICATION TESTS

Blattella germanica 0.5 µl of a solution of the compound in butanone (with or without piperonyl butoxide) was topically applied to male *B.germanica*. Mortality was assessed after 6 days.

The following compounds were active at 101 g or less (+piperonyl butoxide)

5, 14, 15, 17

Musca domestica 0.3 µl of a solution of the compound in butanone (with piperonyl butoxide) was topically applied to female *M.domestica*. Mortality was assessed after 2 days.

The following compounds were active at 1.5 µg or less:

3, 4, 5, 10, 14, 15, 16, 17, 18

| Compound No. | $^1$H NMR Data: |
|---|---|
| 1 | 1.7(1H, m), 2.2(1H, m), 2.7(1H, m), 6.5(3H, m), 7.4(2H, m), 7.5(1H, dd), 7.8(2H, m), 8.3(2H, m), 9.9(1H, s). |
| 2 | 1.6(1H, m), 1.8(1H, m), 2.3(1H, m), 2.3(3H, s), 5.8(2H, m), 6.4(1H, d), 7.0(1H, dd), 7.3(2H, m), 7.5(2H, m), 7.8(1H, s), 8.3(2H, m), 8.6(1H, m). |
| 3 | 1.5(1H, m), 1.8(1H, m), 2.3(1H, m), 2.4(3H, s), 5.8(2H, m), 6.4(1H, d), 7.0(2H, m), 7.5(2H, m), 7.7(1H, m), 8.3(2H, m), 9.6(1H, s). |
| 4 | 1.5(1H, m), 1.7(1H, m), 2.0 and 2.3(3H, s), 2.2 (1H, m), 5.8(2H, m), 6.3(1H, m), 7.0(1H, m), 7.6 (4H, m), 8.4(2H, m), 9.9(1H, s). |
| 5 | 1.6(1H, m), 1.8(1H, m), 2.3(1H, m), 2.4(3H, s), 5.9(2H, m), 6.4(1H, d), 7.0(1H, m), 7.2(1H, m), 7.5(2H, m), 7.7(1H, s), 8.1(1H, m), 8.8(1H, m). |
| 6 | 1.5(1H, m), 1.8(1H, m), 2.2(3H, s), 2.3(1H, m), 5.9(1H, dd), 6.2(1H, d), 6.4(1H, dd), 7.0(1H, dd), 7.5(6H, m), 8.4(1H, m). |
| 7* | 1.8(1H, m), 2.2(1H, m), 2.7(1H, m), 6.5(3H, m), 7.3(2H, m), 7.5(1H, dd), 7.6(1H, d), 7.8(2H, m), 13.0(1H, s). |
| 8 | 1.6(1H, m), 1.8(1H, m), 2.3(1H, m), 2.4(3H, s), 5.9(1H, dd), 6.1(1H, d), 6.5(1H, dd), 6.8(1H, s), 7.0(1H, dd), 7.4(1H, dd), 7.5(2H, m), 8.9(1H, s). |
| 9* | 1.5(1H, m), 1.9(1H, m), 2.4(1H, m), 6.2(4H, m), 7.0(1H, dd), 7.2(1H, dd), 7.5(2H, m), 9.0(1H, s). |
| 10 | 1.6(1H, m), 1.8(1H, m), 2.3(1H, m), 6.0(2H, m), 6.5(1H, dd), 7.0(1H, dd), 7.5(3H, m), 8.2(2H, m), 8.6(1H, m), 8.9(1H, s). |
| 11 | 1.5(1H, m), 1.8(1H, m), 2.3(1H, m), 5.6(1H, b), 6.0(2H, m), 6.6(1H, dd), 7.0(1H, dd), 7.3(5H, m), 8.1(1H, d). |
| 12* | 1.5(1H, m), 1.8(1H, m), 2.3(1H, m), 5.8(1H, dd), 6.2(1H, d), 6.5(1H, dd), 7.0(1H, dd), 7.3(1H, s), 7.4(1H, dd), 7.5(3H, m). |
| 13 | 1.6(1H, m), 1.8(1H, m), 2.4(1H, m), 6.0(2H, m), 6.5(1H, dd), 7.0(1H, dd), 7.3(1H, m), 7.5(2H, m), 9.0(1H, s). |
| 14 | 1.5(3H, m), 2.8(7H, m), 2.0 and 2.3(3H, s), 2.5 (3H, m), 5.6–6.5(3H, m), 7.0(1H, m), 7.5(2H, m). |
| 15 | 1.5(1H, m), 2.8(10H, m), 2.3(3H, m), 5.9(1H, dd), 6.3(1H, s), 6.5(1H, dd), 6.8(1H, d), 7.0(1H, m), 7.3(1H, dd), 7.5(2H, m). |
| 16 | 1.0(6H, m), 2.7(8H, m), 2.3(3H, m), 5.8(1H, m), 6.6(2H, m), 7.0(1H, m), 7.3(1H, m), 7.5(2H, m). |
| 17* | 1.6(1H, m), 1.9(1H, m), 2.4(1H, m), 2.8(4H, m), 3.6(4H, m), 5.8(1H, dd), 6.2(1H, m), 6.4(1H, m), 7.0(2H, m), 7.5(2H, m), 8.5(1H, b). |
| 18 | 1.7(10H, m), 2.3(1H, m), 3.0(4H, m), 5.8(1H, m), 6.4(1H, m), 6.8(1H, d), 7.0(1H, dd), 7.3(1H, dd), 7.5(2H, m). |
| 19 | 1.7(5H, m), 1.8(1H, m), 2.3(1H, m), 2.9(1H, m), 5.8(2H, m), 6.5(1H, dd), 7.0(1H, m), 7.4(1H, m), 7.6(2H, m). |

*denotes $^1$H NMR spectra were obtained in d$_6$-dimethylsulphoxide solutions.

We claim:

1. A compound of the formula:

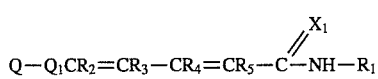

$$Q-Q_1CR_2=CR_3-CR_4=CR_5-\overset{X_1}{\overset{\|}{C}}-NH-R_1$$

where Q is phenyl or naphthyl optionally substituted by
(a) $C_{1-6}$ hydrocarbyl, $C_{1-6}$ alkoxy or methylenedioxy, which in turn is optionally substituted by one to five halogen atoms; or
(b) halo, cyano, nitro; or
(c) a group $S(O)_nR_7$ wherein n=0, 1, or 2 and $R_7$ is $C_{1-6}$ alkyl optionally substituted by halogen, or $R_7$ is amino optionally substituted by one or two $C_{1-6}$ alkyl groups; or a group $NR_8R_9$ where $R_8$ and $R_9$ are independently selected from hydrogen, $C_{1-6}$ alkyl or a group $COR_{12}$ where $R_{12}$ is $C_{1-6}$ alkyl or $C_{1-6}$ alkoxy;

$Q_1$ is a 1,2-cyclopropyl ring optionally substituted by a group selected from $C_{1-13}$ alkyl, halo, $C_{1-3}$ haloalkyl or $C_{1-3}$ alkynyl or cyano;

$R_2$, $R_3$, $R_4$ and $R_5$ are the same or different with at least one being hydrogen and the others being independently selected from the group consisting of hydrogen, halo, $C_{1-4}$ alkyl or $C_{1-4}$ haloalkyl;

$X_1$ is oxygen or sulfur;

$R_1$ is a saturated 6 membered heterocycle containing a nitrogen atom which is bound to NH through a nitrogen atom;

or a pesticidally, insecticidally, or acaricidally acceptable salt thereof.

2. The compound (+)-(2E,4E)-N-piperidino-S-[c-2-(3,4-dibromophenyl)-r-1-fluorocyclopropyl]penta-2,4-dienamide.

3. An insecticidal or acaricidal composition comprising an effective amount of a compound of claim 1 in admixture with a carrier, diluent or excipient.

4. A synergized pesticidal composition comprising an effective amount of a compound of claim 3, an oxidase inhibitor synergist and a carrier or diluent.

5. A method for controlling pests which comprises applying to the pest or to an environment susceptible to pest infection an effective amount of a compound according to claim 3.

* * * * *